United States Patent [19]

Weaver et al.

[11] Patent Number: 5,019,034

[45] Date of Patent: May 28, 1991

[54] CONTROL OF TRANSPORT OF MOLECULES ACROSS TISSUE USING ELECTROPORATION

[75] Inventors: James C. Weaver, Sudbury; Kevin T. Powell, Boston; Robert S. Langer, Jr., Newton, all of Mass.

[73] Assignee: Massachusetts Institute of Technology, Cambridge, Mass.

[21] Appl. No.: 331,263

[22] Filed: Mar. 30, 1989

Related U.S. Application Data

[63] Continuation-in-part of Ser. No. 146,343, Jan. 21, 1988, abandoned.

[51] Int. Cl.$^5$ ............................................. A61M 37/00
[52] U.S. Cl. ..................................... 604/20; 604/890.1
[58] Field of Search ............... 604/890.1, 20; 128/798, 128/802

[56] References Cited

U.S. PATENT DOCUMENTS

| | | | |
|---|---|---|---|
| 4,081,340 | 3/1978 | Zimmermann et al. | 204/299 R |
| 4,154,668 | 5/1979 | Zimmermann et al. | 204/299 R |
| 4,220,916 | 9/1980 | Zimmermann et al. | 324/446 |
| 4,250,878 | 8/1981 | Jacobsen et al. | |
| 4,474,570 | 10/1984 | Ariura et al. | |
| 4,557,723 | 3/1985 | Sibalis. | |
| 4,622,031 | 7/1986 | Sibalis. | |
| 4,639,244 | 1/1987 | Rizk et al. | |
| 4,663,292 | 5/1987 | Wong et al. | 435/287 |
| 4,702,732 | 10/1987 | Powers et al. | 604/20 |
| 4,764,473 | 8/1988 | Matschke et al. | 435/287 |
| 4,786,277 | 11/1988 | Powers et al. | 604/20 |
| 4,822,470 | 4/1989 | Chang | 204/299 R |

FOREIGN PATENT DOCUMENTS 2113097 8/1983 United Kingdom.

OTHER PUBLICATIONS

Sloan et al., *J. Am. Acad. Dermatology*, 15:671-684 (1986).
Neumann et al., *J. Membrane Biology*, 10:279-290 (1972).
Zimmermann et al., *Biophysical J.*, 14:881-899 (1974).
Zimmermann, *Biochim. Biophys. Acta*, 375:209-219 (1975).
Zimmermann et al., *Rev. Physiol. Biochem. Pharmacol.*, 105:175-256 (1986).
Neumann et al., *EMBO J.*, 1:841-845 (1982).
Potter et al., *PNAS*, 78:7161-7165 (1984).
Yoneguzzo et al., *Molecular and Cellular Bio.*, 6:703-706 (1986).
Chu et al., *Nucleic Acids Research*, 15:1311-1326 (1987).
Stopper et al., *Biochim. Biophys. Acta*, 900:38-44 (1987).
Toneguzzo et al., *Proc. 9th IEEE/Engineering in Medicine and Biology Society*, 715-716 (1987).
Weaver et al., *Proc. 9th IEEE/Engineering in Medicine and Biology Society*, 708-709 (1987).
Sowers et al., *FEBS Lett.*, 205:179-184 (1986).
Potter, *Proc. 9th IEEE/Engineering in Medicine and Biology Society*, 705-707 (1987).
Lee et al., *Proc. 9th IEEE/Engineering in Medicine and Biology Society*, 712-714 (1978).
Lee et al., *Plastic and Reconstruct Surg.*, 663-671, (Nov. 1987).

*Primary Examiner*—Stephen C. Pellegrino
*Assistant Examiner*—Ralph A. Lewis
*Attorney, Agent, or Firm*—Hamilton, Brook, Smith & Reynolds

[57] ABSTRACT

An electrical process for enhancing and/or controlling transport of molecules across tissue such as human and animal skin is disclosed. The process involves the use of a high voltage, short duration electrical pulses on the tissue surface to produce electroporation. Once this effect has occurred, concentration, pressure or temperature gradients, or iontophoresis can be used to move molecules across the tissue. The process can be repeatedly applied without producing undesirable tissue damage or can be used to purposely cause highly limited tissue damage for the purpose of providing a desired, relatively long term molecular transport pathway. The occurrence of the electroporation effect can be detected by monitoring the tissue for a reversible electrical breakdown, which, along with an enhanced tissue permeability, is the characteristic effect of electroporation.

23 Claims, 2 Drawing Sheets

CONTROL OF TRANSPORT OF MOLECULES ACROSS TISSUE USING ELECTROPORATION

RELATED APPLICATIONS

The present application is a continuation-in-part of U.S. Ser. No. 07/146,343, filed Jan. 21, 1988, now abandoned, entitled "Control of Transport of Molecules Across Tissue Using Electroporation", by James C. Weaver, Kevin T. Powell and Robert S. Langer, Jr.

BACKGROUND OF THE INVENTION

Molecules such as drugs, nutrients and metabolites are not easily transported into, out of and across tissue, because tissue consists of a variety of cells, often of different types, which must be traversed by molecules. A healthy tissue, perfused by blood, is readily supplied with nutrients and often well supplied with blood-borne drugs. Additionally, metabolic products are generally efficiently removed by the circulatory system. Unfortunately, the ability to deliver or remove compounds through tissue surfaces is generally relatively poor. Likewise, the ability to cause or control the delivery of compounds across tissue, from one surface to another, is relatively poor.

The flux of molecular transport through a tissue is a function of the product of the tissue permeability, the driving force and the area of the tissue. In most early attempts to increase the uptake of pharmaceuticals in living organisms, permeability factors have been the focus as a means of increasing flux. These attempts have focused on providing pharmaceutical compounds to regions of tissue having a natural permeability higher than that found naturally in skin. Such relatively high permeability tissues include tissue of the stomach and intestines, rectal tissue, buccal tissue, sinus tissue, lung tissue and the interstitial tissue below the surface of the skin.

The most common method of using highly permeable tissue for pharmaceutical administration is oral ingestion. This method contacts the pharmaceutical to be administered with the highly permeable stomach lining and intestinal walls. While this route is acceptable for a wide variety of drugs, it has drawbacks which render it less than ideal for some drugs and completely unacceptable for others. These drawbacks include the inability to alter the driving force for controlling transport flux, the likelihood of drug breakdown (due to digestive processes) prior to absorption into the bloodstream, and high first pass liver metabolism or liver toxicity.

The most common method for utilizing the highly permeable interstitial tissue below the skin surface to transport pharmaceuticals is by injection, using either a hypodermic needle or an injection gun. While these methods offer the advantage of quickly placing the drug into the patient's interstitial fluids, many patients, especially children, find injection to be a painful and unpleasant experience. Furthermore, for drugs which are administered frequently or continuously, needle injection sites are subject to high rates of infection.

Like injection, in which the skin is physically breached to expose tissue having a greater permeability than that on the surface, drugs can also be administered to interstitial tissue through surface abrasion of the tissue. This method was commonly used in past as the method of smallpox vaccine administration. In addition to the pain and discomfort of this method, abrasion often results in the formation of unsightly scar tissue at the abrasion site.

In some instances, the tissue has a permeability which is high enough for the administration of certain drugs. In these cases, administration can occur by topical application of the drug. This can be accomplished either by rubbing a compound containing the drug onto the skin surface, or by inserting a material containing the drug into a body orifice, as in the case of suppositories. While this method is painless and has found a variety of uses (notably transdermal patches for nitroglycerine and motion sickness drugs) topical application for drug delivery suffers from the slow rate at which transtissue absorption occurs. Thus, for drugs in which it is acceptable to administer low dosages over prolonged periods of time, topical application can prove useful. However, for the vast majority of drugs, this method is not satisfactory due to the low rate at which the drug is absorbed.

The permeability of tissue such as skin can be elevated above its natural state through the use of absorption enhancers. These are generally penetrating solvents, which, when combined with a drug and applied to the skin, greatly increase drug absorption through the skin. An example of one such enhancer is dimethyl sulfoxide (DMSO).

In each of the examples above, tissue having natural or chemically-enhanced high permeability has been utilized as a means of increasing the flux of the transported molecule.

The flux of molecules across tissues can be further enhanced by increasing the driving force on the molecules. Such driving forces include pressure gradients, concentration gradients and pressures such as acoustic pressure. Additionally, the use of external electromagnetic fields, as in the case of iontophoresis, can be used as a means to increase the driving force.

Iontophoresis utilizes an electrical current to drive positive or negative ions into tissue. See, for example, U.S. Pat. No. 4,141,359 (Feb. 27, 1979) of Jacobsen et al.; U.S. Pat. No. 4,250,878 (Feb. 17, 1981) of Jacobsen et al., U.S. Pat. No. 4,474,570 (Oct. 2, 1984) of Ariura et al.; U.S. Pat. No. 4,557,723 (Dec. 10, 1985) of Sibalis; U.S. Pat. No. 4,622,031 (Nov. 11, 1986) of Sibalis; U.S. Pat. No. 4,639,244 (Jan. 27, 1987) of Rizk et al.; and Sloan et al., *J. Am. Acad. Dermatology*, 15, 671–684, 1984; the teachings of which are incorporated herein by reference. In this method, two or more electrodes are placed into contact with the tissue. At least one of the electrodes is a pad of absorbent material soaked with a solution of the drug to be administered. When a low voltage is applied across the tissue, the ions of the drug move to the electrode of the opposite charge, and in so doing penetrate the tissue. Neutral molecules can be moved, although to a lesser extent, by a phenomenon known as solvent drag in the solution. As long as the voltage is applied, the process will continue with transport abruptly decreasing when the driving force of electrical potential is discontinued.

While these are among numerous methods for increased transport molecule flux by altering or selecting tissue to exhibit high permeability and by selecting various driving forces, a need still exists for a method in which molecules can be transported across tissue at a more rapid, controlled rate, but in a manner which significantly damages neither the molecules nor the tissue and which, when used in vivo, produces little pain and discomfort for the patient.

It is known that the permeability of isolated, widely separated, individual cell membranes can be temporarily increased and the electrical resistance decreased by the process of electroporation and the associated phenomenon of reversible electrical breakdown (REB). See, for example, Neumann et al., *J. Membrane Biol.*, 10, 279-290, 1972 (electroporation); and, Zimmermann et al., *Biophysical J.*, 14, 881-899, 1974; Zimmermann et al., *Biochim. Biophys. Acta*, 375, 209-219, 1975; Zimmermann et al., *Rev. Physiol. Biochem. Pharmacol.*, 105, 175-256, 1986; U.S. Pat. No. 4,081,340 (Mar. 28, 1978) of Zimmermann et al; and U.S. Pat. No. 4,220,916 (Sept. 2, 1980) of Zimmermann et al. (reversible electrical breakdown), the teachings of which are incorporated herein by reference. In this method, a solution containing isolated, individual cells and large molecules such as DNA or enzymes are subjected to a high voltage pulse of short duration. When examined after the pulse, some cells are found to contain the large molecules. In cells that take up DNA some expression has been observed. However, the fraction of cells transformed by electroporation is generally found to be small, for example $10^{-5}$ to $10^{-4}$. Better results have been found in a few cases in which about 1% of electroporated cells have shown uptake, DNA transport into the cell nucleus, incorporation, expression and survival. See, for example, Neumann et al., *EMBO J.*, 1, 841-845, 1982; potter et al., *PNAS*, 78, 7161-7165, 1984; Toneguzzo et al., *Molecular and Cellular Bio.*, 6, 703-706, 1986; Chu et al., *Nucleic Acids Research*, 15, 1311-1326, 1987; Stopper et al, *Biochim. Biophys. Acta*, 900, 38-44, 1987; and Toneguzzo et al., *Proc. 9th IEEE/Engineering In Medicine and Biology Society*, 715-716, 1987, the teachings of which are incorporated herein by reference. Additionally, electroporation of isolated red blood cells has shown that approximately 20% of the electroporated cells dramatically change shape from biconcave disks to spheres and take up relatively uncharged dextran molecules. See Weaver et al., *Proc. 9th IEEE/ Engineering in Medicine and Biology Society*, 708-709, 1987, the teachings of which are incorporated herein by reference.

Prior work indicates that only relatively uncharged molecules, such as dextrans, have been readily introduced into, or released from, individual cells by electroporation, and there is some evidence suggesting that charged molecules are difficult to introduce. See, Sowers et al., *FEBS Lett.*, 205, 179-184, 1986, the teachings of which are incorporated herein by reference. Furthermore, he present method of introducing DNA into individual cells by electroporation results in survival of only about 40-80% of the cells. See Potter, *Proc. 9th IEEE/Engineering in Medicine and Biology Society*, 705-707, 1987, the teachings of which are incorporated herein by reference. This survival rate is acceptable if only a few clones are needed.

Previous studies of the behavior of electrically pulsed tissue have often revealed very significant destruction. See, Lee et al., *Proc. 9th IEEE/Engineering in Medicine and Biology Society*, 712-714, 1987; and Lee et al., *Plastic and Reconstruct. Surg.*, 663-671, Nov. 1987, the teachings of which are incorporated herein by reference. There is no evidence to indicate that electrical pulses have been studied as a means of producing electroporation to increase permeability and molecular transport in tissues such as skin.

SUMMARY OF THE INVENTION

This invention pertains to a process whereby it is possible to increase and control transport of molecules across tissues including human and animal skin and muccosal membranes such as rectal, vaginal and buccal membranes using the process of electroporation to increase the tissue permeability. The process can also be used for artificial or cultured tissues, including artificial tissues which are selected or formed to have particular electroporation properties.

This invention further pertains to a process for transporting molecules across tissue comprising the steps of:

(a) applying one or more pulses of electrical energy of sufficient voltage and duration to a region of a tissue in order to cause electroporation, thereby producing a transient increase in tissue permeability; and (b) utilizing a driving force to move molecules across the regions of the tissue undergoing electroporation.

The driving force to move molecules across the permeabilized tissue may be electrical, such as in the case when iontophoresis is used, or it may be another physical or chemical force such as provided by a temperature gradient, a pressure gradient, or a concentration gradient. Additionally, the driving force may comprise acoustic or optical pressure.

Problems of transporting sufficient numbers of molecules into, out of, or across a tissue can be overcome using electroporation, via the transient high permeability state. An effect, repeatedly observed in tissues undergoing electroporation, called reversible electrical breakdown (REB), can be used to provide an indication of the occurrence of electroporation, thereby providing a basis for selecting the magnitude, duration and shape of the electrical pulse or pulses. The transient high permeability state can be used to increase the transport flux of molecules in conjunction with a driving force such as concentration difference and hydrostatic pressure. Thus, for example, the stratum corneum barrier of skin can be circumvented by causing electroporation to occur on the inner walls of hair follicles and sweat ducts, thereby allowing molecular transport into the interstitial fluids underlying the stratum corneum.

An advantage of this process is the ability to increase tissue permeability. This process is also useful for moving molecules whose driving force cannot be increased. Such molecules include, for example, non-ionic molecules or molecules near their saturation concentration. The process can also provide the ability to select operating conditions that result in little or no permanent effect on the tissue caused by the temporary or transient increased tissue permeability of the process.

DETAILED DESCRIPTION OF THE INVENTION

The phenomenon of electroporation is characterized by several sub-phenomena, including a transient high permeability state and reversible electrical breakdown (REB). REB is characterized by a decrease in the electrical resistance of a tissue which is caused by brief exposure to an abnormally high transtissue potential. Electroporation has been observed in artificial planar bilayer membranes stretched across a macroscopic opening in materials such as poly(tetrafluoroethylene), as well as in cell membranes wherein cells are either punctured with a microelectrode or suspensions of cells are exposed to an external electrical field. REB has been demonstrated and studied using either the artificial bilayer membrane or, a micropunctured cell, and in cell suspensions using a version of a Coulter counter. In contrast, the present invention is useful for producing and utilizing the effects of electroporation in both plant and animal tissue, and is based on a transient high permeability state. The invention can be used with or without detection or measurement of the REB phenomenon occurring at the beginning of the high permeability state.

Electroporation in some or all of the cells in a region of a tissue is caused by short, high voltage electrical pulses applied to the tissue surface or to an underlying tissue region resulting in a transient state of increased tissue permeability. A decreased electrical resistance associated with REB is a further result of electroporation and can be used as an effective means of monitoring electroporation effects.

These results can be demonstrated in a tissue by producing electroporation (and REB) in the following manner:

Short electrical pulses of $10^{-8}$ to 1 sec, or preferably $10^{-6}$ to $10^{-3}$ s, are applied to a tissue sample. At a fixed pulse width, the resistance of the sample will remain virtually unchanged as the voltage magnitude of electrical pulses is increased. Above a certain threshold, however, the resistance rapidly decreases, with higher voltage pulses further decreasing the tissue resistance. This is the characteristic demonstration of electroporationinduced REB, which previously has been demonstrated only for artificial planar bilayer membranes, for micropunctured cells, or for bacteria in a Coulter counter which simultaneously flows isolated cells and an electrical current through an insulating orifice.

Following REB, the transtissue resistance can gradually recover to its initial value. This is similar to previous work on artificial bilayer membranes or individual cell membranes, wherein recovery times have been found to range from microseconds in the case of artificial planar bilayer membranes up to minutes, or more in the case of biological membranes. Furthermore, unlike the case in which longer pulses of lower voltage magnitude are applied to an artificial bilayer membrane, REB caused by electroporation often avoids membrane rupture or irreversible electrical breakdown.

The transmembrane potentials associated with electroporation and REB are in the range of about 500 to about 1,500 mV. This is much higher than the normal physiological resting potential of about 100 mV and generally above the magnitude of transmembrane potentials known to result in membrane rupture (about 300 to 600 mV). Thus, the relatively short duration of the electrical pulses used to induce electroporation and REB is a key aspect of the process. Previous studies of electroporation have observed the effect only in individual cells such as red blood cells, squid axons, squid eggs, and giant algae cells. The present invention shows that electroporation can be demonstrated in multilayer tissues such as living frog skin, rat skin and underlying tissue, hairless mouse skin and underlying tissue, and in surgically removed human skin and underlying tissue. Electroporation can also be demonstrated in artificial tissues, or cultured tissues. The term "artificial" is meant to apply to aggregates of cells which are grown, or cultured (i.e., serially propagated), which function as a tissue, but are not actually derived, or excised, from a pre-existing source or host. Artificial tissues can be grown in vivo or in vitro. For example, human skin can be grown or cultured in vitro to provide a layer of confluent cells, of monolayer thickness or greater, which can function as skin tissue in culture or when grafted onto a living host. The term "tissue" as used herein refers to tissues actually excised from or associated with an animal or plant, and to artificial tissues as defined hereinabove.

Generally, for cells, the occurrence of electroporation, as evidenced by REB, results in non-thermal, short term membrane changes, with all damage or death occurring only due to long term osmotic pressure differences, or other physiochemical imbalances between the inside and outside of a cell experiencing the high permeability state. However, it may be possible to provide conditions, such as iso-osmotic bathing solutions, which minimize tissue damage.

Alternatively, if it is desired to kill or permanently damage some of the cells in order to provide a longer-lasting molecular transport pathway in tissue, a combination of electrical pulse conditions and bathing solution conditions can be selected to result in some cell lysis. For example, an extreme case relates to delayed, non-thermal tissue damage associated with electrocution accidents, wherein it is now appearing that the undesirable aspects of electroporation phenomena can result in significant tissue destruction.

Damage of tissue by cell lysis and by cell fusion can occur for some pulse conditions which induce electroporation and REB. However, it has been demonstrated that electroporation can repeatedly be produced in tissue without causing any significant cell lysis, and while cell fusion has not been investigated directly, no harmful effects attributable to cell fusion have been discovered. Thus, repeated electroporation, as demonstrated through the occurrence of REB of biological tissue, can be essentially harmless to the tissue itself, or to the organism in the case of in vivo induced electroporation.

The fact that electroporation can be repeatedly produced in animal tissue to increase permeability without damaging the tissue is advantageous in that it allows electroporation to be used as a method to increase molecular transport into and/or across biological membranes. A tissue consisting of living cells can be regarded as a multilayered series of individual sheets. Electroporation can be produced in any single sheet by applying a short (i.e., 1–1,000 us) pulse of about 1 to 3 volts across the sheet. This results in electroporation of cells in the sheet, which can be revealed by the occurrence of REB, and allows, through the temporary high permeability state, increased molecular transport through the sheet.

A more complex tissue can be approximated as a multilayered series of such individual sheets. Because a single sheet requires approximately 0.1 to 5 volts and preferably 1 to 3 volts to achieve increased molecular transport, a thicker membrane (e.g., approximately 20 sheets) would require a pulse of, at most, about 20 to about 60 volts and is less when electroporation occurs first at one layer, such that the full potential difference then appears across the remaining layers. This higher voltage itself does not, however, damage the tissue because on the scale of the individual cell layer, it is between only 1 and 3 volts.

Essentially all previously published information regarding electroporation, particularly the occurrence of a high permeability state, and also the detection and measurement of REB, has been obtained from studies on artificial planar bilayer membranes, or from widely separated cells which are suspended in an aqueous electrolyte medium. Based on these studies on non-tissue samples, electroporation is believed to be caused by a temporary creation or enlargement of pores present in an artificial bilayer or cell membrane caused by a sudden intense pulse of transmembrane potential. The enlarged pore size results in greatly decreased electrical and molecular transport resistance across the membrane. Following electroporation, the enlarged pores gradually return to their normal size, resulting in a resistance which gradually increases to its initial value. While the pores are enlarged, however, it is possible to transport both charged ions and neutral molecules across the cell membrane using conventional transport driving forces such as iontophoresis, concentration differences and pressure differences. Once the pore size has decreased to the initial state, the process may be repeated to provide further transport.

An important application of molecule transport into and through tissue relates to non-invasive interstitial fluid chemical assays, and to drug delivery across the skin.

Transdermal pharmaceutical delivery has traditionally been problematic due to the presence of the stratum corneum. The stratum corneum is a sheet of essentially dead cells which exist on the outside of the skin. Both sweat gland ducts and hair follicles interrupt the stratum corneum essentially by perforating it. Dry stratum corneum is well known to be relatively impermeable to water soluble substances. As such, the outermost skin layer, consisting of dry stratum corneum, does not readily lend itself to a process in which the pores of hydrated membranes are enlarged. Thus, it would appear that electroporation is not compatible with transdermal drug transport.

Problems of this type are overcome, however, by the previously discussed fact that the stratum corneum is interrupted by both sweat gland ducts and hair follicles. Often some fluxes of drugs can be iontophoretically passed across the skin without use of electroporation, but increased fluxes of drugs can be diffusively, convectively (by pressure) or iontophoretically moved through sweat gland ducts if the barrier between the interior of the ducts and the interstitial fluid is made more permeable. This is precisely the effect observed on the cell lining of the duct when electrical pulses characteristic for causing electroporation, which can be detected by the occurrence of REB, are applied to the skin.

Furthermore, early studies suggest that barriers such as sweat ducts and especially duct linings are preferentially susceptible to permeability modification by electroporation when electrical pulses are applied to the skin surface. This is due to the fact that the sites of primary resistance to delivery of water soluble molecules are also the sites of the major electrical resistance. The result is that electrical pulses applied from relatively distant electrodes will produce the largest transmembrane potential difference changes of tissue cells at the very site at which electroporation permeability increase is most desired. In the case of sweat gland ducts, and other structures which have the attribute of a tube lined by cells connected by tight junctions, the local relatively high electrical resistance results because of both the approximate cylindrical geometry of the duct, and because of the relatively high electrical resistance of a cell layer with cells connected by tight junctions.

Thus, in practice, an electrical pulse characteristic of inducing electroporation, detected by measuring the occurrence of REB, can be applied to the skin surface. This results in electroporation of cell membranes at the tissue comprising the walls of the sweat ducts. Conventional iontophoresis, concentration difference or pressure difference techniques can then be used as a driving force to transport pharmaceuticals across the sweat duct wall and into the interstitial fluids lying beneath the stratum corneum. Hair follicles may be approached in a manner similar to that of sweat glands. Depending on the state of activity of the sebaceous glands, the hair follicles may offer a second pathway for transdermal drug delivery.

Likewise, a process similar to the above can be used for non-invasive sampling of interstitial fluid for chemical assay. The only significant difference is that outward driving forces, such as negative pressure, can be applied to the skin surface, so as to draw out small amounts of interstitial fluid through the molecular transport pathways caused, or increased in permeability by electroporation.

In one embodiment of the invention, non-polarizable electrodes, such as conventional electrocardiograph electrodes constructed from conventional silver/silver chloride contacting a gel or paste, such as physiological saline, are used. Alternatively, electrodes constructed of stainless steel, platinum or gold can be used. At least one of the electrodes is located in close proximity to a reservoir containing the compound whose transport into or across the tissue is desired. Alternatively, for non-invasive sampling, the transport of endogenous tissue compounds can be altered by locating a collection region or chamber near at least one of the electrodes.

In another embodiment of the present invention, electroporation can be utilized to alter the permeability of artificial tissues. For example, a layer of confluent cells is provided, of monolayer thickness or greater, which is a barrier to the transport of molecules. The layer of cells can be cultured from animal or plant cells of a selected type, e.g., human or animal skin, blood vessel tissue, esophogeal tissue, or membranes, such as buccal, mucosal or intestinal membranes. The barrier provided by the artificial tissue can be altered by the present electroporation process; that is, by the application of electrical fields, potentials and/or currents so as to cause electroporation of at least one cell in the layer of cells. The layer of cells constitutes an artificial tissue, which can be formed from one or more types of cells which are particularly effected by electroporation.

Artificial tissues can be selected or formed to have desirable electroporation properties. Thus, artificial tissues can be provided having certain electroporation properties, which can be used for drug delivery or for non-invasive sampling, as described above; or for other purposes, such as studying the transport of certain molecules across selected types of tissues using electroporation without the necessity of obtaining samples from human or animal hosts. Artificial tissues have been described, for example, by Yannas et al. in U.S. Pat. No. 4,458,678, Bell et al. in U.S. Pat. No. 4,485,096 and Green et al. in U.S. Pat. No. 4,304,866.

An example of an artificial tissue combined with means for causing electroporation is a delivery system comprising an artificial blood vessel with nearby implanted electrodes or reservoir for introduction into, or sampling from, the vessel. Specifically, electroporation of the artificial tissue of such, a vessel can rapidly add drugs or other chemical compounds into the blood, such that systemic delivery could be rapidly accomplished. In addition to utilizing cells selected according to criteria related to usual blood vessel function, some or all of the cells comprising the artificial tissue can be selected particularly for use with electroporation, with desirable properties such as allowing high levels of transcellular transport because of electroporation, having a desired cell membrane recovery time and/or having the ability to experience repeated electroporation while experiencing relatively little cell damage or cell death compared to normal blood vessel tissue.

It is also possible to incorporate cells selected for their electroporation properties into artificial tissues which serve as skin replacements or substitutes. Such an artificial skin tissue can be implanted in order to serve as a site for introducing or removing molecules through the use of electroporation, thereby providing means for drug delivery or interstitial fluid composition sampling.

A source of electrical potential, capable of generating a series of short electrical pulses of the type sufficient to induce electroporation is connected to at least two electrodes, allowing potentials of suitably short duration. In one embodiment, the pulses are approximately "square wave" in nature, with a duration of width ranging from about $10^{-8}$ s to about 1 s. In other embodiments, the pulses are saw tooth, triangular, exponential or sine wave in nature, again with a duration of width ranging from about $10^{-8}$ s to about 1 s. In the preferred embodiment, pulse width ranging from about $10^{-6}$ s to about $10^{-3}$ s is used to produce REB and thereby to indicate the occurrence of electroporation.

The magnitude of the pulses is selected to correspond to that needed to produce electroporation and REB across the particular tissue being energized. Generally this voltage will be in the range of about 20V to about 2,000V, with a range of about 50V to about 750V being more likely. When the tissue contains many cell layers as in the case of human skin, these voltages, applied for short periods, produce a transmembrane potential of about 0.5V to about 3V on each cell layer. The voltage actually selected will depend upon the tissue properties of the electroporation site, which, in the case of human skin, for example, can vary significantly depending on age, fat content and location on the body.

Figure 1:
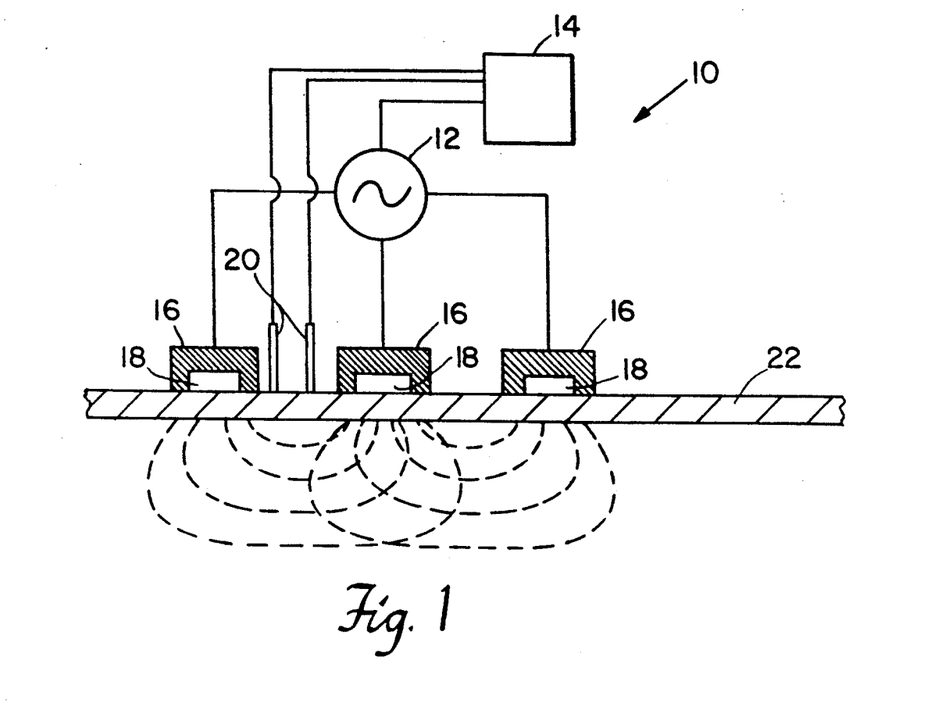
FIG. 1 is a schematic representation of an apparatus useful for transporting molecules across a tissue using enhanced tissue permeability induced by electroporation.

One embodiment of an apparatus for producing the transient high permeability state in tissue via electroporation for the purpose of drug delivery is represented schematically in FIG. 1. In FIG. 1, the apparatus, represented generally as 10, comprises an electrical pulse generator 12, a controller 14, a set of two or more electrodes 16, of which at least one has a molecule reservoir 18, and optionally, a means 20 for detecting REB.

In operation, the reservoirs 18 are filled with the molecules to be transported and the electrodes 16 are placed in contact with the surface of tissue 22. A pulse generator 12, in communication with the electrodes 16 provides an electrical pulse of a specific shape, voltage, duration and frequency to the electrodes. The shape, duration, frequency and peak voltage of the pulse are controlled by a controller 14. The pulse is gradually cycled to higher voltages until electroporation occurs. At that point, the pulse, shape, duration, frequency and voltage is maintained until a desirable amount of molecular transfer has occurred.

Optionally, a second set of electrodes 20, or the same electrodes 16, can be used to monitor electrical resistance through the tissue. These electrodes 20 are operatively connected to the controller 14 and serve as a means for detecting the reversible electrical breakdown occurring during electroporation Thus, they serve to inform the controller 14 of the point at which pulse conditions should be maintained.

Figure 2:
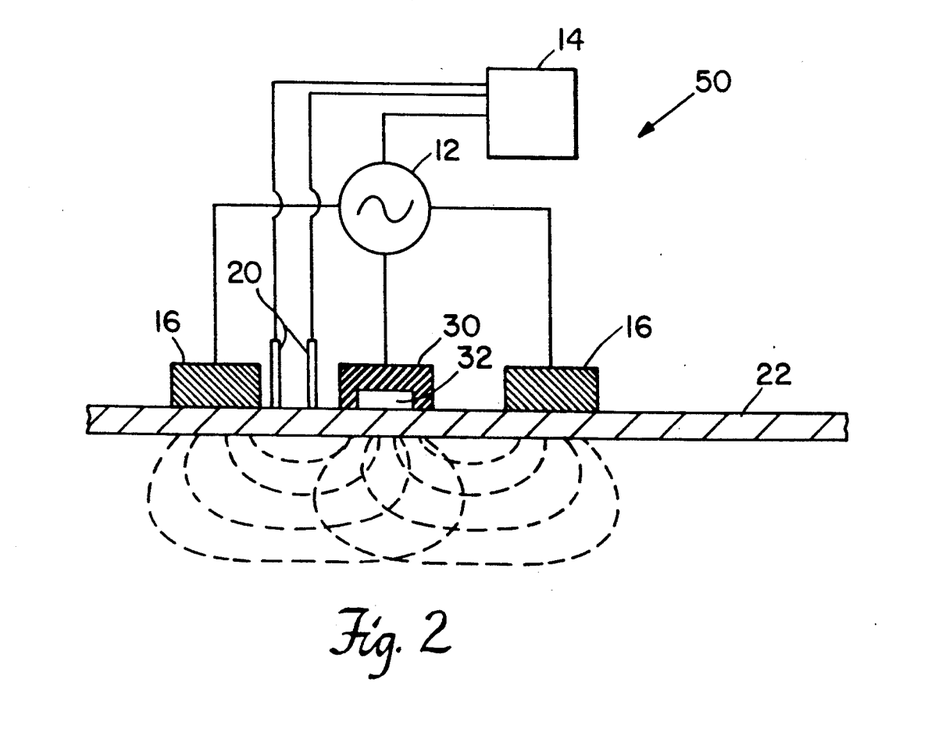
FIG. 2 is a schematic representation of an apparatus useful for transporting interstitial fluids to the surface of a tissue using enhanced tissue permeability induced by electroporation.

Another embodiment of the invention, a diagnostic apparatus, is represented schematically in FIG. 2. In FIG. 2, the apparatus, represented generally as 50, comprises an electrical pulse generator 12, a controller 14, a set of two or more electrodes 16, a container 30, optionally an electrode, having a reservoir 32, and optionally, a means 20, for detecting REB.

The apparatus operates much like that of the previous embodiment, except that instead of being useful as a means for delivering a drug, apparatus 50 is useful as a non-invasive means for collecting interstitial fluids for diagnostic purposes.

In operation, the electrodes 16 are placed in contact with the surface of tissue 22. A pulse generator 12, in communication with the electrodes 16, and optionally with an electrode-container 30, provides an electrical pulse of a specific shape, duration, voltage and frequency to the electrodes. The shape, duration, voltage and frequency of the pulse are controlled by a controller 14. The pulse is gradually cycled to higher voltages until electroporation occurs. At that point, the high permeability state allows interstitial fluids to be transported out of the tissue into the reservoir 32 of container 30. These interstitial fluids can then be used in a variety of diagnostic procedures.

A second, optional set of electrodes 20, operates in the same manner as in the previous embodiment.

In both FIGS. 1 and 2, the drug-containing or fluid-collecting container can be either an electrode or an electrically neutral container. For example, in some embodiments, the container can be electrically neutral and used in conjunction with electrodes which may or may not contain reservoirs, while, in other embodiments, the container can be incorporated into an electrode which is used in conjunction with other electrodes which may or may not contain reservoirs. Optionally, non-energized containers can be used with an electrode-container as well. As such, the embodiments of the invention are not intended to be limited to those represented by FIGS. 1 and 2.

In yet another embodiment of the apparatus, reservoirs for the transport of molecules into tissue and for the collection of molecules transported out of tissue can be employed simultaneously. As described previously, either or both types of reservoirs can be incorporated into electrodes or can be electrically neutral and used in conjunction with charged electrodes. Such an embodiment provides the ability to use one pulse generator and controller to simultaneously produce both therapeutic and diagnostic electroporation in tissue.

In the preferred process of this invention, the values and changes in values of the electrical impedance between any pair of electrodes, either during or after any pulse or pulse series, are monitored to allow a determination of the occurrence of REB for any tissue transport situation. More specifically, by monitoring the electrical impedance between any pair of electrodes, preferably using a low level alternating current with a frequency between 100 Hz and 10,000 Hz, the mass transport resistance associated with low molecular weight ionic species such as $Na^+$ and $Cl^-$, which occur at naturally high concentrations in biological tissues, can be used to indicate the occurrence of REB and thereby, the occurrence of electroporation and the associated high permeability state.

Because the transdermal pharmaceutical delivery method, or interstitial fluid sampling, is controlled directly by electrical means, it is possible to program a method for precisely controlling delivery which takes into account differences in individual skin properties, and differences in individual drug delivery or interstitial fluid sampling needs. For example, the pulse generator can be programmed to produce short, low voltage pulses of increasing magnitude while monitoring for the occurrence of REB. The potential of the pulses is gradually incremented to a higher level until REB is detected. At this point, the generator can supply pulses at this level, while constantly monitoring for any change in REB, making adjustments accordingly to maintain the condition. This allows the electroporation process to be precisely controlled, while actively avoiding an electrical condition capable of causing undesirable tissue damage.

Once REB has been detected, pharmaceutical compounds can be transported across cell membranes using a conventional driving force. For example, in one embodiment of the invention, electroporation is induced in the membranes lining the interior of sweat ducts. The pharmaceutical is then transported through these membranes into the interstitial fluids underlying the stratum corneum surface.

Similarly, once REB has been detected, conventional methods, such as negative pressure, can be used to acquire interstitial fluid samples.

A number of methods for transport of molecules across the electroporated membranes are possible. Each of these methods uses a driving force to move molecules across the temporarily permeabilized membrane. For example, in one simple method, a concentrated form of the material to be transported is held in a reservoir contacting the tissue surface at the site of electroporation. The driving forces of concentration difference in combination with an externally elevated hydrostatic pressure causes the material to pass through the enlarged tissue cell membrane pores into the underlying interstitial fluids. Once the pores have gradually retracted to their initial diameter, or a diameter below which the transport rate is too low, a new electric pulse is applied to the area to repermeabilize the tissue cell membranes.

In another embodiment, iontophoresis can be used as the driving force to transport molecules across the tissue once enhanced permeability through electroporation has occurred. In this embodiment, a pulse is applied to a site in order to increase permeability by inducing electroporation. Simultaneously with, or subsequent to the detection of REB, an electrical potential of much lower voltage and greater duration is applied to the electroporated site. Ions present in this low voltage field will migrate toward sources of opposite charge. Thus, if an electrode is present at another distant site, oppositely charged drug ions will migrate through the electroporated membrane into the subcutaneous, interstitial fluids. Neutral molecules can also be moved via iontopheresis by a phenomenon known as solvent drag. This results from the repeated contact of charged particles moving in one direction, such that net transport of a neutral molecular species occurs because of the transport of the electrically charged species. As with concentration difference or pressure difference transport, the transport site is monitored to detect pore retraction or cell membrane recovery. When the pores have retracted to a size at which the transport rate drops below a selected level, the continuous, low voltage field for the iontophoresis is temporarily interrupted or is maintained and a new electrical pulse having the characteristics to induce electroporation is applied.

The transport processes associated with this invention lend themselves to use with a wide variety of molecules including drugs and molecules of diagnostic interest. As used herein, the term "drug" is broadly defined to include any chemical agent that affects or prevents processes in a living organism. Examples include drugs which are intended for therapy such as antibiotics, drugs which are intended for prevention such as polio vaccine, and drugs which are intended for diagnosis. Similarly, molecules of diagnostic interest include both naturally occurring species such as metabolites, hormones and proteins as well as therapeutically introduced molecules.

Additionally, electroporation has been demonstrated to insert large molecules, such as enzymes and DNA, into individual cells. Thus, it is expected that this method can be used to transport comparably large molecules into and/or across tissues, including particularly the skin.

The following examples are intended to more specifically illustrate the present invention.

EXAMPLE I

Electrical Effects

A fresh excised piece of abdominal frog skin was placed in a diffusion apparatus as a membrane between two chambers. Each chamber was filled with frog Ringer's solution comprising 100 mM NaCl, 2 mM KCl, 2 mM $CaCl_2$, 2.4 mM $NaHCO_3$ and 10 mM dextrose. The following electrical properties were measured:

| | |
|---|---|
| Resistance | R = 500–1000 Ohm/cm$^2$ |
| Capacitance | C = 0.5–5 Farad/cm$^2$ |
| Short Circuit Current | $I_{sc}$ = 5–50 uA |
| Resting Potential | $V_{oc}$ = −20 to −100 mV (mucosal side ground) |

Each of these values was found to be in agreement with standard accepted values.

Planar stainless steel electrodes were used to apply pulses, and the resistance of the skin sample was monitored using calomel electrodes or Ag/AgCl electrodes to detect the increased permeability state of electroporation and REB. REB was demonstrated in three ways.

Figure 3:
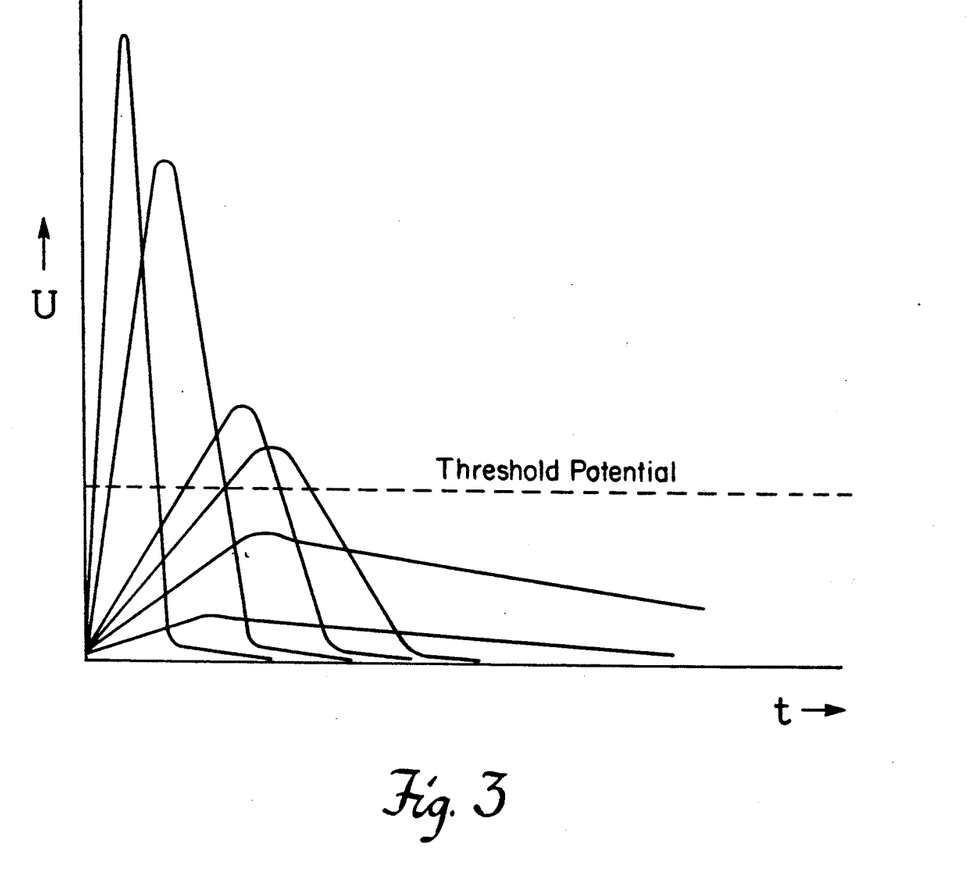
FIG. 3 is an arbitrary graphic representation of electrical potential versus time for a series of electrical pulses of varying potential and duration when applied to a tissue.

In the first REB demonstration, electrical pulses of varying magnitude and duration were applied. Post-pulse decay of the transdermal potential was faster when pulses above threshold magnitudes or above threshold durations were applied. When decaying transdermal potentials were recorded on an oscilloscope, the traces cross when sub- and supra-threshold pulses were applied. This effect is clearly seen in FIG. 3. As skin capacitance is a relatively constant value, the change in rate of electrical potential decay indicated decreased electrical resistance and corresponding increased ionic permeability of the frog skin.

In the second REB demonstration, the data for the decaying transdermal potentials of the above experiment were digitized and curve fit. The results quantified the change in resistance as occurring as a threshold event. The transdermal resistance was found to be most dependent upon the maximum transdermal potential produced by the applied pulse. It was seen that when the potential for the pulse was above a certain threshold, a large decrease in transdermal resistance was created.

In a third REB demonstration, low level current ramps were repeatedly applied to the skin, producing a real time measurement of skin resistance. After a single, high voltage pulse was applied (with the injected charge increasing skin potential to 1-2 volts), the transdermal resistance dropped 50-75%. A drop of this magnitude is an indication that the skin's permeability to small ions increased between 100 and 300%, that is, an increase by a factor of two to four.

In each of these experiments, frog skin was used. Frog skin, electrically, is approximately a monolayer of cells. The applied pulses varied from 1.0 to 200V with a duration varying from 1.0 to 1000 us. These conditions produced a charge injection that raised the transdermal potential between 0 and 2V. A single pulse which produced a transdermal potential greater than the 0.5–1.5V threshold was correlated with the appearance of the high permeability (REB) state. The increased permeability was transient, decreasing to its normal level after about 10–120 seconds. The effect was repeated on the tissue sample over 100 times without apparent damage.

Similar studies were conducted on tissue supplied from hairless mice, rats and human cadavers. All samples showed similar evidence of increased ion permeability (as measured from reduced electrical resistance) after pulses of high electrical potential were applied to the sample. While none of the mammalian tissue samples showed as dramatic a resistance decrease as frog skin, the effect was still seen in each case. This is likely due to the fact that unlike frog skin, the mammalian tissue consists of a series of tissue layers rather than a single layer.

EXAMPLE 2

Control for Radioisotope Effects

Excised sections of hairless mouse skins were placed in a diffusion chamber with liquid baths on both sides. One of the liquid baths was "hot", i.e., it contained radiolabelled C-14 L-glucose. (Normal sugar is D-glucose, also referred to as dextrose.) The cold, or "sink" side, of the mouse skin was sampled. The data was most consistent with non-specific binding of the L-glucose onto the skin surface. The L-glucose skin binding prevents molecular transfer across the skin. Thus, this control serves to demonstrate one of the problems which this invention is contemplated to overcome.

EXAMPLE 3

In Vitro Rat Tests

Two in vitro rat experiments were perfomed using 1 uCi H-3 mannitol and 10 mM unlabelled mannitol on the hot bath side. Adjacent skin samples were taken from the rat, using one as the control sample and the other as the test sample. The test sample was treated with electroporative pulses of 80V and 4.5 uS duration at 0.5 Hz during hours 4–11 of the experiment. After a six hour lag time, the pulsed skin had 30% greater flux than the control. It should be noted, however, that the statistical validity of the effect cannot be determined from one experiment.

The permeability of the test sample was about $4 \times 10^{-8}$ cm/sec. This is about 270 times less than the in vivo case, demonstrating the effect of having to transfer the mannitol through the whole skin thickness rather than the much shorter distance from the skin surface to the capillary bed.

EXAMPLE 4

In Vitro Frog Tests

Two in vitro frog experiments were performed in a similar manner to the rat experiments. Pulsing was 20V, 100 uS, at 0.24 Hz. Within 1 hour after pulsing, the pulsed skin's permeability increased 4 fold over both its own baseline permeability and that of the control skin. This increased permeability was maintained for 12 hours, but damage occurred to the skin and the increase was not reversible in this experiment.

EXAMPLE 5

In Vivo Rat Tests

Two in vivo experiments using H-3 mannitol were performed on rats. 10 uCi of the H-3 mannitol were painted on skin. Urine was collected and measured. In the control rat, a constant flux without lag was observed over 36 hours. In the second rat, the skin was pulsed with a 1 Hz square wave of 80V magnitude and 1 uS duration during hours 28 to 34 of the experiment. This pulse was 2-10x that required to produce REB in in vitro experiments, but the circuit in vivo was different, and ion permeability could not be measured. Due to sporadic urine output, the result appears positive but some ambiguity remains. The overall permeability of the pulsed skin setup was about 3% of applied dose absorbed per day.

EQUIVALENTS

Those skilled in the art will recognize, or be able to ascertain, using no more than routine experimentation, many equivalents to the specific embodiment of the invention described herein. Such equivalents are intended to be encompassed by the following claims.

We claim:

1. A method for transporting molecules across tissue comprising the steps of:
   a. applying at least one electrical pulse of sufficient voltage and duration to a region of tissue, wherein the tissue comprises at least a single layer of cells, in order to cause electroporation in the region; and b. utilizing a driving force to move molecules across the regions of the tissue undergoing electroporation.

2. A method of claim 1, wherein the tissue is selected from the group consisting of animal tissue and plant tissue.

3. A method as in claim 2, wherein the animal tissue comprises skin.

4. A method as in claim 3, wherein the skin comprises human skin.

5. A method as in claim 2, wherein the animal tissue is selected from the group consisting of buccal, vaginal and rectal membrane.

6. A method as in claim 2, wherein the tissue is artificial tissue.

7. A method as in claim 2, wherein a high permeability state caused by the electroporation is used to increase and control molecular transport through the walls of sweat ducts or hair follicles.

8. A method as in claim 1, wherein the driving force is electrical force.

9. A method as in claim 8, wherein the driving force is iontopheresis.

10. A method as in claim 1, wherein the driving force is a non-electrical physical or chemical force.

11. A method as in claim 10, wherein the driving physical force is selected from the group consisting of: pressure gradients, and concentration gradients.

12. A method as in claim 1, wherein the transported molecules comprise a pharmaceutical.

13. A method as in claim 1, wherein the transported molecules comprise a compound of diagnostic interest.

14. A method as in claim 1, further comprising the step of monitoring the electrical resistance of the tissue in order to determine the occurrence of reversible electrical breakdown.

15. A method as in claim 14, wherein the measurement of the reversible electrical breakdown is used to provide an indication of the occurrence of electroporation.

16. A method as in claim 15, wherein the measurement of reversible electrical breakdown is used to provide an indication of the occurrence of electroporation to a means capable of automatically controlling pulse voltage and duration as well as time between pulses when more than one pulse is applied.

17. A method as in claim 14, wherein electrical resistance of the tissue is determined from the reversible electrical breakdown measurement, said electrical resistance being used to estimate the change in the permeability of the tissue.

18. A method as in claim 1, wherein the electrical pulse is of sufficient voltage and duration to produce a permanent, high permeability condition in some cells of the tissue undergoing electroporation.

19. A method as in claim 18 in which the electrical resistance of the tissue is monitored in order to determine the occurrence of a permanent high permeability condition is some cells of the tissue undergoing electroporation.

20. A method as in claim 1, wherein the electrical pulse is selected from the group consisting of square wave pulses, saw tooth pulses, triangular wave pulses, exponential wave pulses and sine wave pulses.

21. A method for temporarily increasing the permeability of tissue which comprises applying at least one electrical pulse of sufficient voltage and duration to a region of tissue, wherein the tissue comprises at least a single layer of cells, said method further characterized by the occurrence of reversible electrical breakdown in the electroporated region and wherein the electroporated region is used as a site of molecular transport.

22. A method as in claim 21, wherein a driving force is used to increase molecular transport at the electroporated region.

23. A method as in claim 22, wherein the driving force is selected form the group consisting of pressure gradients, concentration gradients, and iontophoresis.

* * * * *

REEXAMINATION CERTIFICATE (2654th)
United States Patent [19]
Weaver et al.

[11] B1 5,019,034
[45] Certificate Issued   Aug. 15, 1995

[54] CONTROL OF TRANSPORT OF MOLECULES ACROSS TISSUE USING ELECTROPORATION

[75] Inventors: James C. Weaver, Sudbury; Kevin T. Powell, Boston; Robert S. Langer, Jr., Newton, all of Mass.

[73] Assignee: Massachusetts Institute of Technology, Cambridge, Mass.

Reexamination Request:
No. 90/003,252, Nov. 9, 1993

Reexamination Certificate for:
Patent No.: 5,019,034
Issued: May 28, 1991
Appl. No.: 331,263
Filed: Mar. 30, 1989

Related U.S. Application Data

[63] Continuation-in-part of Ser. No. 146,343, Jan. 21, 1988, abandoned.

[51] Int. Cl.⁶ ............................................. A61M 37/00
[52] U.S. Cl. .................................... 604/20; 604/890.1
[58] Field of Search ............... 604/20, 890.1; 128/798, 128/802; 435/173.5, 173.6, 172.3

[56] References Cited

U.S. PATENT DOCUMENTS

| | | | |
|---|---|---|---|
| 3,614,955 | 10/1971 | Mirowski | 128/419 D |
| 3,680,544 | 8/1972 | Shinnick et al. | . |
| 4,081,340 | 3/1978 | Zimmermann et al. | 204/299 R |
| 4,154,668 | 5/1979 | Zimmermann et al. | 204/299 R |
| 4,220,916 | 9/1980 | Zimmermann et al. | 324/446 |
| 4,250,878 | 8/1981 | Jacobsen et al. | . |
| 4,474,570 | 10/1984 | Ariura et al. | . |
| 4,557,723 | 3/1985 | Sibalis | . |
| 4,622,031 | 7/1986 | Sibalis | . |
| 4,639,244 | 1/1987 | Rizk et al. | . |
| 4,663,292 | 5/1987 | Wong et al. | 435/287 |
| 4,702,732 | 10/1987 | Powers et al. | 604/20 |
| 4,764,473 | 8/1988 | Matschk et al. | 435/287 |
| 4,786,277 | 11/1988 | Powers et al. | 604/20 |
| 4,822,470 | 4/1989 | Chang | 204/299 R |
| 4,923,814 | 5/1990 | Marshall, III | 435/173 |
| 5,128,257 | 7/1992 | Baer | 435/173 |

OTHER PUBLICATIONS

Okino et al, "Electrical Impulse Chemotherapy for Rat Solid Tumors," *Jap. J. Cancer Res.*, 46:420 (1987).

Okino et al, "Intracellar Bleomycin Concentration and Histological Examination in Electrical Impulse Chemotherapy," *J. Jap. Soc. for Cancer Therapy*, 22(8):377 (1987).

Okino et al, "Effects of a High-Voltage Electrical Pulse and an Anticancer Drug on In Vivo Growing Tumors," *Jap. J. Cancer Res.*, 78(12):1319–1321 (1987).

Kanesada et al, "Anticancer Effects of Electrical Impulse Chemotherapy for the Primary and Metastatic Foci of Lewis Lung Carcinoma," *J. Jap. Soc. for Cancer Therapy*, 22(8):338 (1987).

Zerbib et al., "Electric Field Mediated Transformation: Isolation and Characterization of a TK⁺ Subclone," *Biochem. & Biophys. Res. Comm.*, 129(3): 611–618 (1985).

*Primary Examiner*—Mark Bockelman

[57] ABSTRACT

An electrical process for enhancing and/or controlling transport of molecules across tissue such as human and animal skin is disclosed. The process involves the use of a high voltage, short duration electrical pulses on the tissue surface to produce electroporation. Once this effect has occurred, concentration, pressure or temperature gradients, or iontophoresis can be used to move molecules across the tissue. The process can be repeatedly applied without producing undesirable tissue damage or can be used to purposely cause highly limited tissue damage for the purpose of providing a desired, relatively long term molecular transport pathway. The occurrence of the electroporation effect can be detected by monitoring the tissue for a reversible electrical breakdown, which, along with an enhanced tissue permeability, is the characteristic effect of electroporation.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATIN, IT HAS BEEN DETRMINED THAT:

claims 2–5, are cancelled.

claim 1, 6–8, 14, 17–19 and 21 are determined to be patentable as amended.

New claim 24 is added and determined to be patentable.

1. A method for transporting molecules across *skin* tissue comprising the steps of:
   a. applying at least one electrical pulse of sufficient voltage and duration to a region of *skin* tissue, wherein the *skin* tissue comprises at least a single layer of cells, in order to cause electroporation *through the layer of cells of the skin tissue* in the region; and
   b. utilizing a driving force to move molecules across the regions of the *skin* tissue undergoing electroporation.

6. A method as in claim [2] *1*, wherein the *skin* tissue is artifical *skin* tissue.

7. A method as in claim 1, wherein a high permeability state caused by the electroporation is used to increase and control molecular transport through the walls of sweat ducts or hair follicles.

8. A method as in claim [2] *1*, wherein the driving force is electrical force.

14. A method as in claim 1, further comprising the step of monitoring the electrical resistance of the *skin* tissue in order to determine the occurrence of reversible electrical breakdown.

17. A method as in claim [14] *15*, wherein electrical resistance of the *skin* tissue is determined from the reversible electrical breakdown measurement, said electrical resistance being used to estimate the change in the permeability of the *skin* tissue.

18. A method as in claim 1, wherein the electrical pulse is of sufficient voltage and duration to produce a permanent, high permeability condition in some cells of the *skin* tissue undergoing electroporation.

19. A method as in claim 18 in which the electrical resistance of the *skin* tissue is monitored in order to determine the occurrence of a permanent high permeability condition [is] *in* some cells of the *skin* tissue undergoing electroporation.

21. A method for temporarily increasing the permeability of *skin* tissue which comprises applying at least one electrical pulse of sufficient voltage and duration to a region of *skin* tissue, wherein the *skin* tissue comprises at least a single layer of cells, *in order to cause electroporation through the layer of cells in the region*, said method further characterized by the occurrence of reversible electrical breakdown *of the skin tissue* in the electroporated region and wherein the electroporated region is used as a site of molecular transport *across the skin tissue*.

*24. A method of claim 1, wherein human skin tissue is electroporated.*

* * * * *